(12) United States Patent
Kurowski et al.

(10) Patent No.: US 7,357,016 B2
(45) Date of Patent: Apr. 15, 2008

(54) PROCESS AND DEVICE FOR DETERMINING VISCOSITY

(75) Inventors: Dirk Kurowski, Schwelm (DE); Christian Schoen, Dortmund (DE); Ralf-Peter Peters, Bergisch-Gladbach (DE); Holger Bartos, Dortmund (DE); Ying Yu, Dortmund (DE)

(73) Assignee: Boehringer Ingelheim microParts GmbH, Dortmund (DE)

( * ) Notice: Subject to any disclaimer, the term of this patent is extended or adjusted under 35 U.S.C. 154(b) by 0 days.

(21) Appl. No.: 11/014,192

(22) Filed: Dec. 17, 2004

(65) Prior Publication Data

US 2005/0155415 A1 Jul. 21, 2005

(30) Foreign Application Priority Data

Dec. 17, 2003 (DE) ............................. 103 59 438
Feb. 25, 2004 (DE) ..................... 10 2004 009 089

(51) Int. Cl.
 *G01N 11/10* (2006.01)

(52) U.S. Cl. .................... 73/54.41; 73/54.24; 73/54.25

(58) Field of Classification Search ............... 73/54.42, 73/54.24, 54.25, 54.26, 54.27
See application file for complete search history.

(56) References Cited

U.S. PATENT DOCUMENTS

| 3,650,698 | A |   | 3/1972  | Adler           |          |
|-----------|---|---|---------|-----------------|----------|
| 3,861,197 | A |   | 1/1975  | Adler           |          |
| 3,967,934 | A |   | 7/1976  | Seitz et al.    |          |
| 4,648,262 | A | * | 3/1987  | Reis et al.     | 73/54.18 |
| 4,864,849 | A |   | 9/1989  | Wright          |          |
| 4,876,069 | A |   | 10/1989 | Jochimsen       |          |
| 4,918,984 | A | * | 4/1990  | Martinoli et al.| 73/64.43 |
| 5,025,656 | A | * | 6/1991  | Wright          | 73/32 A  |
| 5,110,727 | A |   | 5/1992  | Oberhardt       |          |

(Continued)

FOREIGN PATENT DOCUMENTS

DE 197 35 931 2/1999

(Continued)

OTHER PUBLICATIONS

Simon et al., "Diamagnetically Stabilized Magnet Levitation", pp. 702-713, 2001.

(Continued)

*Primary Examiner*—Michael Cygan
(74) *Attorney, Agent, or Firm*—David S. Safran

(57) ABSTRACT

A process and a device for determining the viscosity of a fluid are proposed. Very simple and accurate determination is enabled in that the magnetic particles in the fluid are set into vibration by a magnetic field which varies over time. A measurement of the amplitude and/or phase of particle vibration is used to determine the viscosity or an associated quantity, such as the coagulation of blood or the glucose content.

38 Claims, 5 Drawing Sheets

U.S. PATENT DOCUMENTS

| | | | |
|---|---|---|---|
| 5,140,161 A | | 8/1992 | Hillman et al. |
| 5,350,676 A | * | 9/1994 | Oberhardt et al. ............ 435/13 |
| 5,394,739 A | * | 3/1995 | Garvey et al. ............. 73/54.23 |
| 5,629,209 A | * | 5/1997 | Braun et al. .................. 436/69 |
| 5,841,023 A | * | 11/1998 | Parker et al. .............. 73/53.01 |
| 5,975,153 A | | 11/1999 | Hill et al. |
| 6,018,988 A | * | 2/2000 | Persson ..................... 73/54.25 |
| 6,136,271 A | | 10/2000 | Lorincz et al. |
| 6,591,664 B2 | | 7/2003 | Litton |
| 6,767,511 B1 | * | 7/2004 | Rousseau .................... 422/73 |
| 6,880,384 B2 | * | 4/2005 | Hvidtfeldt et al. ......... 73/64.56 |

FOREIGN PATENT DOCUMENTS

| | | |
|---|---|---|
| DE | 197 45 807 | 5/1999 |
| DE | 101 30 727 | 1/2003 |
| DE | 103 09 132 | 9/2004 |
| JP | 8-178823 | 7/1996 |
| WO | WO 01/86255 | 11/2001 |

OTHER PUBLICATIONS

M. Keller et al., "Oscillatory Magnetic Bead Rheometer of Complex Fluid Microrheometry", Review of Scientific Instruments, vol. 72, No. 9, pp. 3626-3634, 2001.

BBC News Health, Home Blood Tests 'Accurate as Hospital', file: //M:\SCHOEN\P203_CoaguChip\Berichte\Presse\Homeblood tests'accurate as hospital'.html, Oct. 29, 2003.

Prinzip der Lock-In-Detektion am Beispiel eines ESR Signals.

"Low-Field Magnetic Sensing with GMR Sensors" of Carl H. Smith and Robert W. Schneider, Nonvolatile Electronics, Inc., pp. 2-13, 1999.

J. Schotter, et al. Comparison of a Prototype Magnetoresistive Biosensor to Standard Fluorescent DNA Detection, pp. 1-20.

"Technologieanalyses Magnetismus Band 2, XMR-Technologien" of VDI-Technologiezentrum Physikalische Technologien, pp. 1-80.

\* cited by examiner

PROCESS AND DEVICE FOR DETERMINING VISCOSITY

BACKGROUND OF THE INVENTION

1. Field of Invention

This invention relates to a process and a device for determining the viscosity or an associated quantity of a fluid or of magnetic particles in a fluid, especially of a microfluid, and uses of such a process or such a device.

2. Description of Related Art

U.S. Pat. No. 3,967,934 discloses a system and process for determining the coagulation time of blood. A test tube with blood is moved up and down, a metal ball in the blood within the test tube being kept in a vertical position by means of a steady-state magnetic field. When the test tube is moved up and down the blood flows around the metal ball. When coagulation of the blood takes place, the metal ball is deflected out of its defined vertical position. This deflection activates a photoelectric barrier and this is acquired as the coagulation time. The system is very complex, and in particular,r moving parts are necessary. The process is not suited for microfluidics, i.e., samples with a small volume, especially in the range of one milliliter or less. Likewise, no information about the progression of coagulation available.

Japanese patent publication JP 8-178823 discloses a process and a device for measuring the viscosity of viscous material. The measurement elements are fine, soft-magnetic particles, which are moved by an external steady-state magnetic field in the viscous material, for example, silicone or acrylic resin, in one direction. By means of a sensor which is based, for example, on the magnetoresistive effect, information about the moving magnetic particles is detected and the velocity and time of movement are measured to determine the viscosity. Compared to measurement elements which settle otherwise only by gravitation, a much shorter measurement time of roughly two to five minutes can be achieved. In the known process, the disadvantage is that several attempts with the addition of magnetic particles, which is necessary at the time, are needed in order to be able to achieve reasonable measurement accuracy. The process is accordingly complex and tedious. The process is not suited for microfluidics, i.e., samples with a small volume, especially in the region of one milliliter or less. Nor is any information about the progression of coagulation available.

SUMMARY OF THE INVENTION

A primary object of this invention is to devise a process and a device for determining the viscosity or an associated quantity of a fluid or of microscopic particles in the fluid, especially of a microfluid, and applications of this process and this device, a simple, compact structure and/or accurate determination of the viscosity or an associated quantity being enabled, and especially the viscosity and the associated quantity can be continuously determined.

The aforementioned object is achieved by a process in which at least one magnetic particle is moved in a fluid by means of an inhomogeneous magnetic field, the at least one magnetic particle is set into vibration and translational movement back and forth by variation of the magnetic field over time, the at least one magnetic particle is focused or held magnetically in a three-dimensional area within the fluid, at least one of the amplitude and phase of the vibration are magnetically measured and at least one of the viscosity, and the associated quantity or attenuation of the particle vibration is determined therefrom.

The aforementioned object is achieved by a device having a measurement chamber for holding the fluid with at least one coil for producing an inhomogeneous magnetic field which varies over time, so that at least one magnetic particle within the fluid, which particle is completely surrounded by the fluid, can be set into translational vibration within the fluid, and a sensor means or measurement means for magnetic detection of the particle vibration having a measurable amplitude and/or phase for determining the viscosity and/or the associated quantity or the attenuation of particle vibration.

It is a further object to use the device and process to ascertain the coagulation capacity of blood for nontherapeutic purposes from the viscosity by adding a coagulation agent to fluid and to use the coagulation capacity to determine the glucose concentration.

It is also an object of the invention to use the device and process for determining the mobility of particles or the attenuation of movement of particles in a fluid in order to determine the attachment, especially of atoms or molecules, to the particles in the fluid, or the detachment of the particles.

The underlying idea of this invention is to cause at least one magnetic particle in the fluid to vibrate by time variation of a magnetic field so that the particle which is completely surrounded by the fluid floats freely in the fluid without guidance, therefore without mechanical guidance in the fluid or in the measurement chamber, the amplitude and/or the phase of vibration being at least indirectly measured in order to determine therefrom the viscosity or an associated quantity, such as the Reynolds number, the Strouhal number or the like. This enables simple and accurate determination of the viscosity and the associated quantity, especially a compact and simple structure, preferably without mechanically moving parts, and continuous determination of the viscosity with high precision being enabled. The "phase of the vibration" is the phase shift of the vibration of the particles relative to the magnetic field which varies (excites) over time, briefly summarized here.

The viscosity need not be determined directly or absolutely. Rather, it can be sufficient, if necessary, to determine the viscosity only in relative terms or to determine a quantity which is functionally, especially unambiguously associated with the viscosity or depends on the viscosity.

The term "viscosity" in this invention, in a narrower sense, is defined as inner friction or the possibility of accommodating tension in the deformation of a fluid, especially a liquid. In a broader sense, "viscosity" or an associated quantity is also defined as a change of the properties of a possibly inhomogeneous fluid, especially by coagulation, swelling of components or the like, and/or properties of particles, especially their mass, magnetic moment, or mobility or the attenuation of particle vibration, in the fluid, for example, by attachment or detachment of atoms or molecules to or from particles or the like, or changes in this respect.

The process of the invention and the device in accordance with the invention can be used especially for nontherapeutic processes for determining the coagulation capacity of blood or blood plasma, for determining the attachment of atoms and molecules to the magnetic particles or detachment therefrom or for determining the glucose concentration, the viscosity of a fluid being determined which, for example, is linked to the blood via a membrane which is permeable to glucose and with its viscosity dependent on the glucose concentration.

Other advantages, features, properties and aspects of this invention result from the following description of preferred embodiments using the drawings.

DETAILED DESCRIPTION OF THE INVENTION

In the figures, for the same or similar parts the same reference numbers are used, the corresponding or comparable properties and advantages being achieved, even if a repeated description is omitted.

In an inhomogeneous magnetic field a magnetic dipole experiences a force along the field gradient. Accordingly magnetic particles can be moved within the fluid by means of an inhomogeneous magnetic field. By varying the magnetic field over time the magnetic particles are caused to vibrate as claimed in the invention. The device as claimed in the invention and the process as claimed in the invention are based on this principle.

Then, as claimed in the invention, an at least indirect measurement of the amplitude and/or phase of vibration of the particles takes place. They depend on the attenuation of particle vibration and therefore constitute a measure of the viscosity or other properties of the fluid and/or the particles. Accordingly the viscosity, especially in the aforementioned broad sense, or an associated quantity of the fluid or of the particles, can be determined.

The viscosity need not be determined directly or absolutely. Rather it can be sufficient to determine the viscosity only in relative terms or to determine a quantity which is functionally, especially unambiguously associated with the viscosity or depends on the viscosity.

Figure 1:
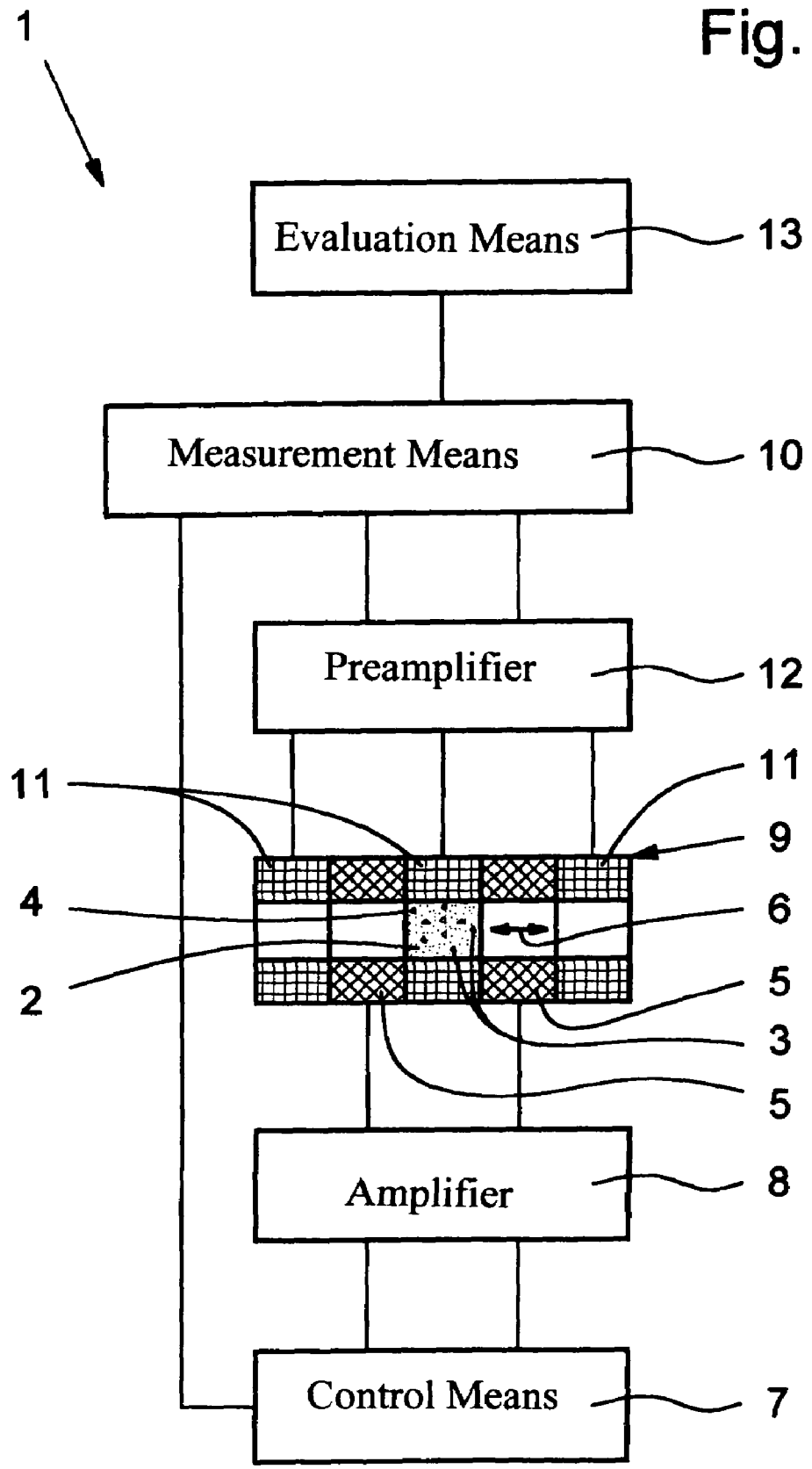
FIG. 1 is a schematic block-like diagram of the device in accordance with the invention according to a first embodiment.

FIG. 1 shows in a schematic a device 1 as claimed in the invention according to a first embodiment for determining the viscosity or an associated quantity of a fluid 2.

The fluid 2 is preferably a liquid, especially for biological or chemical tests or diagnostics.

The volume of the fluid which is to be measured can be very small and is preferably only in the μl range. In particular it is therefore especially a so-called microfluid.

The fluid 2 has at least one magnetic particle 3, especially several magnetic particles 3. Several magnetic particles 3 are described each time below. All statements in this respect in general apply accordingly, even if there is only a single particle 3 in the fluid 2.

Preferably the magnetic particles 3 are added only to the necessary measurement volume of the fluid 2 or only in one area of space or one local measurement area so that the required number of magnetic particles 3 is low. But the particles 3 can also be distributed in the entire fluid 2.

The particles 3 contain preferably iron oxide, especially magnetite or other ferrite. But the particles 3 can also contain other suitable magnetic materials.

The particles 3 are preferably superparamagnetic. This means that they have a magnetization curve which corresponds to ferromagnets, but have no remanence.

But basically other magnetic, especially paramagnetic or ferromagnetic particles 3, can be used.

The magnetic particles 3 preferably have a jacket, especially of plastic.

The particles 3 are made preferably at least essentially granular, spherical and/or ellipsoidal.

The particles 3 are preferably made at least essentially spherical. The average diameter of the particles 3 is preferably 20 nm to 1000 microns, especially roughly 100 nm to roughly 500 microns and quite especially preferably roughly 0.5 microns to roughly 100 microns.

Preferably particles 3 with an at least essentially uniform shape and/or size or the same average diameter are used.

The particles 3 are freely floating in the fluid 2, therefore are arranged especially without mechanical guidance in the fluid 2. The density of the particles 3 preferably corresponds at least essentially to the density of the fluid 2 or is preferably greater than the density of the fluid 2. The fluid 2 permanently surrounds the particles 3—at least the particles 3 relevant to the measurement—completely.

The device 1 has a measurement chamber 4 for holding the fluid 2 and the particles 3. The device 1 furthermore has at least one electromagnetic coil 5, in the illustrated embodiment two coils 5, for producing a magnetic field 6 which varies over time in the measurement chamber 4 or in a measurement region thereof. In particular the measurement chamber 4 is located between the spaced coils 5 and/or is surrounded by them.

In the illustrated embodiment a control means 7—especially with two oscillators or function generators with amplitudes, frequencies, phases, and/or offset which is or are adjustable—and optionally an amplifier 8 which is connected in between, are assigned to the two coils 5 in order to produce periodic, preferably sinusoidal magnetic fields which have been phase-shifted especially by 90°, by means of the coils 5.

The magnetic fields which have been produced by the coils 5 are added to the inhomogeneous magnetic field 6 which is acting on the particles 3 and which varies in time, preferably an alternating field. By means of the magnetic field 6 which varies over time the particles 3 are caused to vibrate, in back and forth motion, therefore translational movements.

The device 1 is preferably made such and the triggering of the coil or coils 5 producing the magnetic field 6 takes place preferably such that the particles 3 execute an induced, preferably at least essentially sinusoidal vibration.

The device 1 has a sensor means 9 and a measurement means 10 in order to magnetically detect the motion—therefore vibration—of the particles 3 in the fluid 2 and to measure the amplitude and/or the phase of the vibration.

In the illustrated embodiment the sensor means 9 has at least one measurement coil 11, especially several measurement coils 11. In particular there are a total of three measurement coils 11, their being arranged preferably in pairs on opposing ends of a coil 5 and being wound oppositely. This is used for compensation of the magnetic fields which are produced by the coils 5 so that the vibration of the particles 3 can be more easily detected and measured.

In the illustrated embodiment, the middle measurement coil 11 for the two coil pairs, in the representation according to FIG. 1, is used both for the right and also for the left coil pair. This saves a fourth measurement coil 11. But basically there can also be a fourth measurement coil 11 for forming two separate measurement coil pairs.

When a vibration is detected by means of the coils 11 especially the induced voltage is measured which is a function of the frequency, the amplitude and the magnetic moment of the particles 3.

The signals of the measurement coils 11 are output directly, or if necessary, as shown in FIG. 1, via a preamplifier 12 to the measurement means 10. The preamplifier 12 can be used for example for electronic compensation of the measurement coils 11 and/or for impedance matching or the like.

The measurement means 10 determines and measures the amplitude and/or the phase of the vibration of particles 3 in the fluid 2. In particular, to determine the phase, more accurately the phase shift relative to the excitation field or magnetic field 6 acting on the particles 3, the control means 7 if necessary can transmit a corresponding synchronization or reference signal to the measurement means 10, as indicated in the illustrated embodiment by a corresponding connection in FIG. 1.

The measurement means 10 works especially according to the so-called lock-in process and preferably has a so-called lock-in amplifier.

The measurement means 10 can alternatively or in addition to the preferred lock-in process or in some other way also measure the amplitude and/or phase of the vibration of the particles 3 in the fluid 2.

The amplitude can be measured absolutely for example after the corresponding calibration. But it can also be measured in relative terms, for example the time characteristic or the time change of the amplitude over time. This time characteristic constitutes for example a measure of the progression of coagulation for example in the coagulation of blood as a fluid 2.

The amplitude and phase of particle vibration depend on the attenuation and thus on the viscosity. The viscosity and/or an associated quantity of the fluid 2 and/or of the particles 3 is determined from the measured amplitude and/or phase. This takes place especially by an evaluation means 13, especially a computer or the like.

The viscosity and the associated quantity can preferably be displayed and/or can be output via an interface which is not shown here, for example for further processing.

The sensor means 9 can have, instead of measurement coils 11, in addition or alternatively, another magnetic and/or electrically operating sensor for detection of the vibration of particles 3. For example the sensor can be a GMR (giant magneto-resonance), TMR (tunnel magneto-resonance), AMR (anisotropic magneto-resonance) or a magnetoresistor, a magnetoimpedance, a Hall sensor or the like. In particular the vibration of the particles 3 due to magnetic effects, influences, or properties is detected. For example in so-called XMR sensors, such as GMR sensors, or in Hall sensors, by measuring the magnetic stray field the vibration amplitude can be determined. But the sensor can optionally also work acoustically, capacitively or inductively.

In the first embodiment the two coils 5 preferably produce periodic, especially at least essentially sinusoidal magnetic fields which are preferably phase shifted by the control means 7, especially phase-offset by 90°. The diagram shown in FIG. 2 which is only schematic provides only a rough approximation for the middle between the coils 5 and shows the time characteristic of the two magnetic fields which are produced by the coils 5 and which are shown as lines 14 and 15 with an amplitude which has been normalized to a value of 1.

Figure 2:
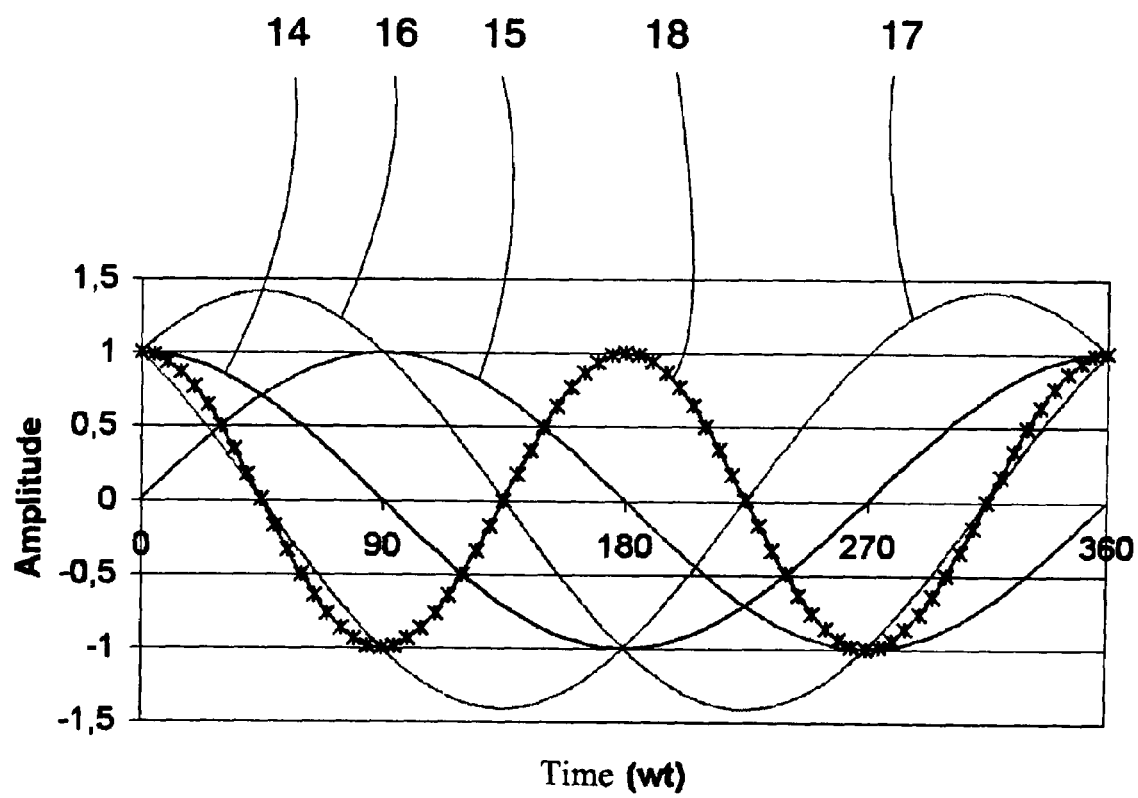
FIG. 2 is a schematic phase diagram of varying magnetic fields and a force acting on magnetic particles.

The two magnetic fields produced by the coils 5 are added to one another to form the inhomogeneous magnetic field which varies in time, which acts on the particles 3, and which is shown in FIG. 2 as the line 16.

It should be noted that the particles 3, at least when they are superparamagnetic, always experience a force in the direction of the stronger magnetic field regardless of its polarization, therefore in the direction of the three-dimensional field gradient. This can be attributed to the fact that at least superparamagnetic particles 3 align their magnetic moments always in the direction of the magnetic field 6 such that they are attracted to the (stronger) coil 5 which produces the magnetic field 6.

In FIG. 2 line 17 shows the three-dimensional leakage of the magnetic field 6 between the two coils 5, the change in the location of the particles 3 by their vibration, proceeding from an only very small vibration amplitude, having been ignored. The multiplication of the two curves 16 and 17 yields the line 18 which is a measure of the force which has been produced by the magnetic field 6 and which acts on the particles 3. Here it should be noted that the characteristic of the force acting on the particles 3 has twice the frequency of the magnetic field 6. Accordingly the particles 3 in the first embodiment vibrate with twice the excitation frequency.

Based on twice the vibration frequency of the particles 3 relative to the magnetic field 6 which changes or varies over time, especially for the preferred lock-in process, noise signals which originate especially from (different) magnetic susceptibilities are at least largely masked, since they do not show the doubled frequency, but only the excitation frequency. As the measurement signals of the measurement means 10, especially of the lock-in amplifier which evaluates the doubled excitation frequency, signals of the vibration of the particles 3 and signals based on the susceptibilities of the particles 3 are formed.

The measurement (measurement signal $\propto$ amplitude frequency/distance$^4$ of the particle vibration) of the amplitude and/or of the phase of particle vibration is thus comparatively simple. The result constitutes a measure of the attenuation of the particle vibration in the fluid 2 and thus of the viscosity in the indicated sense. With the corresponding calibration and/or for example a comparison measurement which proceeds at the same time, accordingly the viscosity and/or an associated quantity of the fluid 2 and of the particles 3 can be determined in the explained sense from the amplitude and phase.

In the first embodiment essentially only the alternating field which is formed by the magnetic field 6 acts on the magnetic particles 3. This can be implemented especially when the magnetic particles 3 in the fluid 2 are present relatively uniformly and/or in a sufficient concentration in the relevant measurement region and/or when the particles 3 are held or concentrated by the magnetic field 6 as a result of its inhomogeneity to a sufficient degree in the measurement region.

If conversely in addition an especially steady-state magnetic field is acting on the particles 3—for example for concentration in the measurement range and/or a defined alignment of the magnetic moments, the magnetic moments of the particles 3 are influenced and optionally fixed so that the doubling of the frequency of the vibration of the particles 3 which is provided in the first embodiment compared to the frequency of the alternating magnetic field 6 which varies in time does not occur because the magnetic moments cannot be aligned freely to the magnetic field 6.

Figure 3:
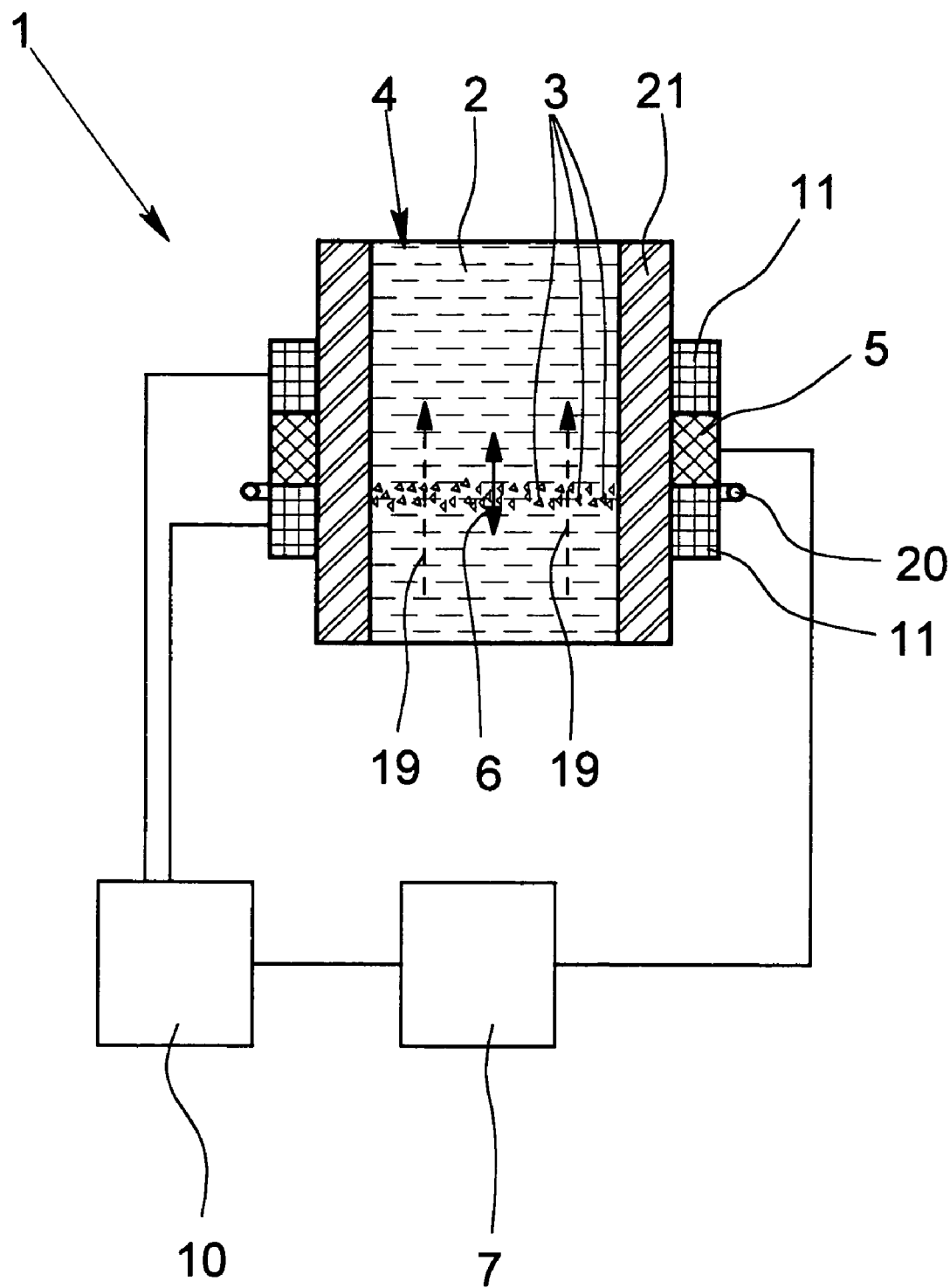
FIG. 3 shows a schematic block-like diagram of the device as claimed in the invention according to a second embodiment.

FIG. 3 shows a second embodiment of the device 1 as claimed in the invention. Only major differences from the first embodiment are explained below. Otherwise the same or at least similar advantages and properties arise.

There is only one coil 5 for producing the magnetic field 6 which varies over time.

But there can also be two coils 5 which are preferably made as Helmholtz coils connected antiparallel. The coils 5 are then wound preferably oppositely so that with sinusoidal excitation the north pole and the south pole of the coils 5 are always aligned to one another. To produce the magnetic field 6 which varies over time only one oscillator or function generator is sufficient based on the opposite windings of the coils 5.

The detection of particle vibration also takes place by the measurement coils 11 in the second embodiment. They are preferably mutually compensated so that the magnetic field 6 of the coil 5 in the ideal case does not produce a signal in the measurement means 10, especially in its lock-in amplifier or the like.

In the second embodiment there is preferably only one or two measurement coils 11. The measurement coils 11 are preferably arranged symmetrically to the coil 5 for compensation of the alternating field 6, the measurement coils 11 radially surrounding the measurement chamber 4.

In place of a measurement coil 11 or the illustrated two measurement coils 11, other sensors can also be used for detection of particle vibration.

In addition or alternatively to the preamplifier 12, an alternating field impedance bridge for negative feedback in the measurement circuit can be connected to increase the measurement sensitivity.

In the second embodiment preferably a stronger magnetic field 19 which is constant in time is superimposed on the inhomogeneous alternating magnetic field 6 of the coil 5. This magnetic field 19 is produced either by an electromagnet—in FIG. 3 by a coil 20 with only one winding or several windings—or by a permanent magnet or ring magnet which is not shown.

The stronger magnetic field 19 is strongest in the plane of the coil 20 and is used to focus the particles 3 in this plane or in the area of the coil 20 or of a magnet which is used alternatively or in addition. To prevent the particles 3 from being drawn to the outside by the coil 20 and optionally by the coil 5 from the middle of the measurement chamber 4 to the wall of the measurement chamber 4, diamagnetic shielding 21 is assigned to the measurement chamber 4 and is located between the particles 3 and the coils 5, 20.

The shielding 21 in the illustrated embodiment is made especially hollow-cylindrical. Optionally it can also completely surround the measurement chamber 4. If necessary the diamagnetic shielding 21 can also be formed directly by the wall of the measurement chamber 4 or can form the measurement chamber 4.

The diamagnetic shielding 21 causes the particles 3 to experience a repulsive force when they approach, therefore they are repelled by the shielding 21. Thus it is possible to focus or keep the particles 3 in an equilibrium position or in a certain region and moreover in the indicated manner to set them into induced vibration, in the illustrated example according to the double arrow 6. The device 1 therefore has a means for holding or focussing the particles 3 especially magnetically in one area of space, preferably the local measurement area within the measurement chamber 4. These means can however if necessary also—optionally exclusively in an alternative manner—be formed by the magnetic field 6 when, depending on the detected location of at least one particle 3, it is controlled such that the particle 3 or several particles 3 is or are held in the local area, preferably the measurement area, at least for a time interval which is sufficient for measurement.

As a result of the magnetic field 19 the direction of the magnetic moment of the particles 3 in space, specifically in the direction of the homogeneous magnetic field 19, is fixed. The weaker magnetic alternating field 6 therefore produces only vibration of the particles 3 with the same frequency. The frequency doubling which was addressed in the first embodiment therefore does not occur here.

The noise signals which are caused especially by the action of magnetic susceptibilities are modulated with the single excitation frequency of the magnetic field 6. Since the particles 3 vibrate with the same frequency, the vibration of the particles 3 can be detected essentially only or most easily by the phase shift relative to the excitation frequency.

The diamagnetic shielding 21 is preferably likewise provided in the first embodiment, but has been omitted for reasons of simplification.

Figure 4:
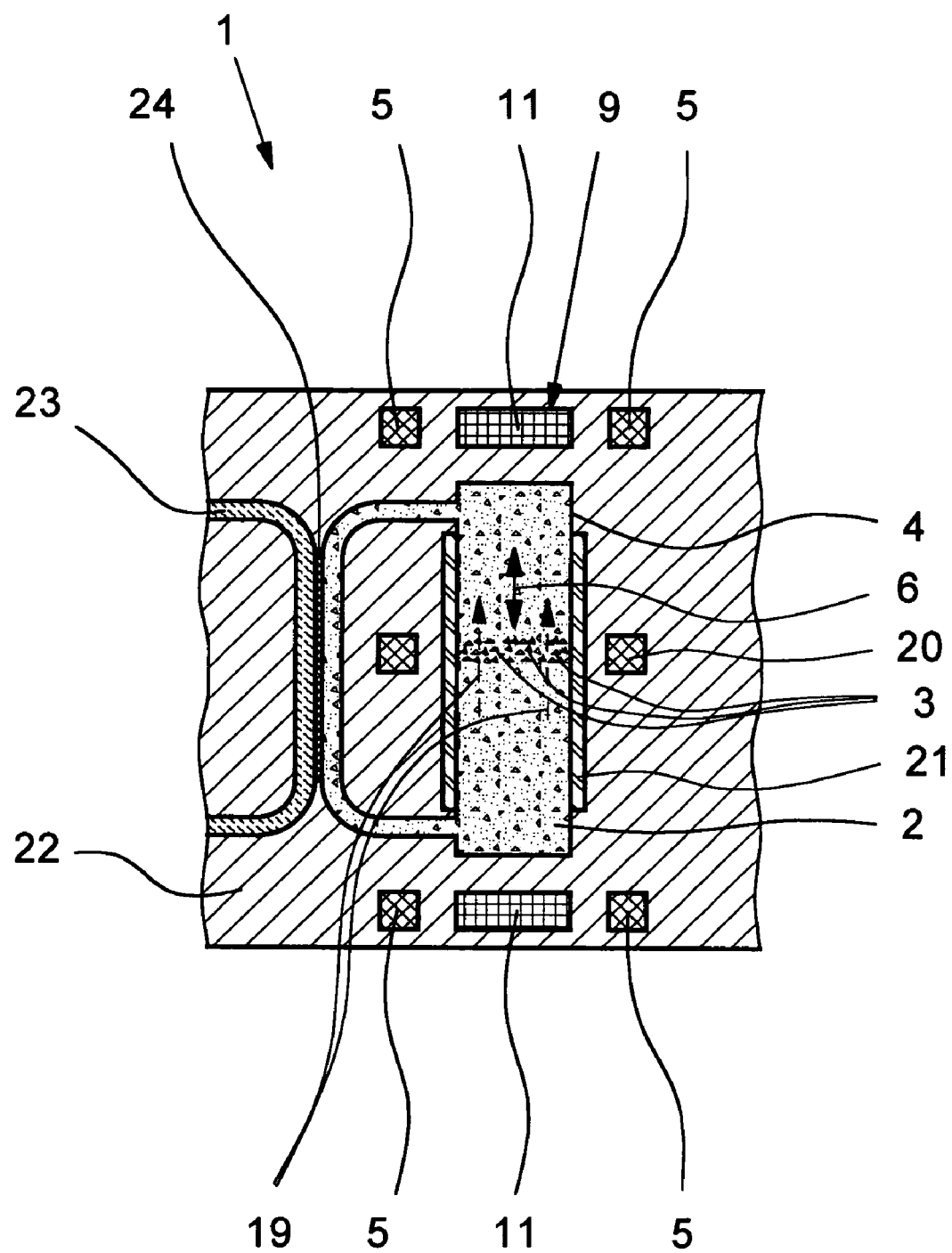
FIG. 4 shows a schematic section of the device as claimed in the invention according to a third embodiment.

FIG. 4 shows in a vertical schematic section a third embodiment of the device 1 as claimed in the invention. Only major differences from the first and/or second embodiment are explained below. Otherwise essentially the same properties, advantages and possible technical implementations arise.

In the third embodiment the measurement chamber 4 is made in a preferably plate-shaped sample carrier 22. The sample carrier 22 consists preferably of plastic, in which the corresponding cavities are formed. For example it can be a test strip or the like which is used especially for chemical and/or biological diagnostics or microfluidic tests.

The measurement chamber 4 is preferably made with the main direction of extension running perpendicular to the plane of the plate of the sample carrier 22. The axes of the coil 5 and the magnetic field 6 which varies over time run preferably in the same direction as the measurement chamber 4, therefore here perpendicular to the plane of the plate of the sample carrier 22.

Therefore the vibration of the magnetic particles 3 takes place preferably at least essentially perpendicularly to the plane of the plate or to the flat sides of the sample carrier 22.

The device 1 and the sample carrier 22 are preferably made such that blood plasma or blood 23 or interstitial liquid can be taken up preferably automatically by capillary forces.

According to a version which is not shown, the blood or blood plasma 23 can be used directly as the fluid 2 and for example can be supplied directly to the measurement chamber 4. In this case the measurement chamber 4 contains preferably magnetic particles 3 and especially a coagulation agent.

After supplying the blood or blood plasma 23, the magnetic particles 3 are distributed in the blood or blood plasma by the acting magnetic fields and/or are concentrated in the measurement region, especially by the steady-state magnetic field 19 of the coil 20, optionally also a certain thorough mixing especially of the coagulation agent which is not shown with the blood or blood plasma 23 can be achieved by the vibration of the particles 3.

The viscosity or an associated quantity, as already explained, especially according to the first or second embodiment, is determined and represents especially a measure of coagulation of the blood and blood plasma 23 in the measurement chamber 4. Accordingly the device 1 in this version is made for direct measurement or determination of the coagulation capacity of blood or blood plasma 23.

In the illustrated embodiment as shown in FIG. 4, the device 1 or the sample body 22 in addition has a membrane 24 which is permeable to glucose. In particular the device 1 can then optionally also take up interstitial liquid instead of blood or blood plasma 23. The fluid 2 is made sensitive to glucose such that the viscosity of the fluid 2 changes depending on the glucose content. For example, the fluid 2 contains high molecular dextran, concanavalin A as affinity receptors for glucose modification thereof and/or other sugar-binding molecules.

The fluid 2 which is in glucose exchange via the membrane 24 with the blood or blood plasma 23 or interstitial liquid can be pumped for example by means of a pump or means which is not shown into the measurement chamber 4 or is circulated through it and past the membrane 24.

In the measurement chamber 4 the viscosity or the associated quantity of the fluid 2, especially according to the first or second embodiment, is determined and the glucose content is determined therefrom.

If necessary the fluid 2 which is sensitive to glucose during the measurement of the amplitude and/or the phase of the vibration of the magnetic particles 3 can continue to be supplied or circulated. For a uniform or at least essentially homogeneous and constant flow of the fluid 2 through the measurement chamber 4 if necessary also only one coil 5 can be used for producing the magnetic field 6 which varies over time, so that the magnetic particles 3 by superposition of the flow and the magnetic force which is acting on it execute vibration in the measurement chamber 4 and within the desired measurement range in order to determine the viscosity and glucose content therefrom.

Figure 5:
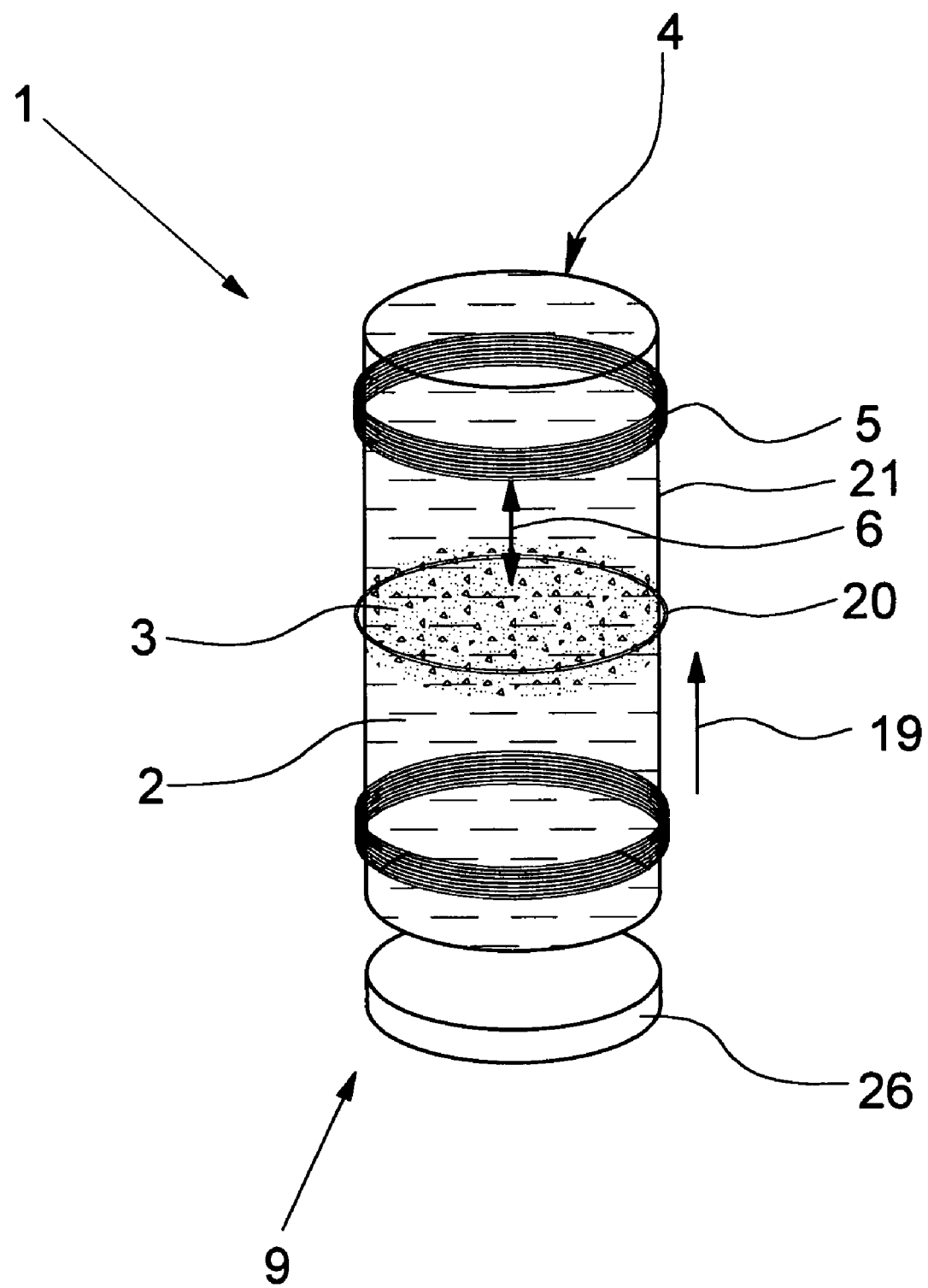
FIG. 5 shows a schematic section of the device as claimed in the invention according to a fourth embodiment.

FIG. 5 shows in a very schematic representation a fourth embodiment of the device 1 as claimed in the invention, below only major differences from the already explained embodiments being emphasized. Otherwise the same or at least similar advantages and properties arise.

The coils 5 for producing the magnetic field 6 which varies over time surround the end areas or are located following the ends of the measurement chamber 4.

Again there is a coil 20 for superposition of the varying magnetic field 6 with the stronger magnetic field 19 which is constant in time.

The static magnetic field 19 therefore in turn—preferably in the central area and/or between the coils 5—forms an inhomogeneity or sink for the particles 3 so that they are held there or concentrated in this region. The additional coil 20 for this purpose is made especially very narrow in the axial direction and optionally is formed only by a single turn. The magnetic field 19 which has been produced by the coil 20 is relatively strong in order to attract the particles 3 into its coil plane.

The varying magnetic field 6 then causes vibration of the particles 3 around the indicated initial or rest position.

The diamagnetic shielding 21 in the fourth embodiment is formed directly by the wall of the measurement chamber 4.

In the fourth embodiment the sensor means 9 instead of the measurement coils 11 has a GMR 26 as a sensor for detection of the particle vibration. In particular a single sensor or GMR 26 is sufficient for detection of the particle vibration, since its resistance or measurement signal varies greatly as a function of the distance of the particles 3 to the GMR 26 and thus correlated to particle vibration. Evaluation can then be done as in the already described embodiments or in some other way.

According to one preferred version the device 1 is operated at least in the area of or at the resonant frequency of the particles 3. Thus a comparatively great amplitude of the particles 3 is achieved at a comparatively low power consumption; this is accessible to measurement of the amplitude and/or phase.

According to one especially preferred version the frequency of the varying magnetic field 6 is permanently varied and/or is preferably automatically controlled or adjusted to the resonant frequency or the frequency with the minimum or maximum amplitude of the particles 3.

By variation of the frequency of the varying magnetic field 6 the amplitude and the phase can be at least relatively determined and changes of these quantities can be detected. Then changes of the viscosity and/or particle properties can be determined therefrom.

Preferably the size and optionally other properties of the particles 3 are determined from the resonant frequency and/or the resonance curve—therefore the dependency of amplitude and/or phase of particle vibration on the frequency of the varying magnetic field 6. This is especially possible for the known properties of the fluid 2 and/or with the corresponding calibration.

Alternatively or in addition, by measurement of the amplitude and/or the phase of particle vibration and/or determination of the resonance curve the mobility of the particles 3 in the fluid and thus for example the attachment or detachment of atoms and molecules to the particles 3 or from the particles 3 can be qualitatively and optionally quantitatively fixed or determined.

According to another embodiment, particles 3 of different size are used, especially at least two sizes of particles 3. Preferably then selectively or in succession in the area of different resonant frequencies for the two particle sizes the amplitude and/or phase of particle vibration is measured.

It follows from the aforementioned that the process as claimed in the invention and the device 1 as claimed in the invention are universally suited for measurement of the viscosity or an associated quantity of the fluid 2, especially a liquid or particles 3, especially also determination or detection of the coagulation capacity of blood or blood plasma 23 or the detection of glucose content being enabled. The process as claimed in the invention and the device 1 as claimed in the invention are especially suited for use in microfluidic systems.

As already explained at the beginning, the term "viscosity" in this invention is defined in a narrower sense as inner friction or the capability of the fluid 2 to accommodate tension during deformation. In a broader sense "viscosity" is defined as the change of properties of the optionally inhomogeneous fluid 2, especially by coagulation or swelling or dissociation of components or the like, and/or a change of the flow properties or other properties of the particles 3 in the fluid 2, for example by attachment of atoms or molecules to the particles 3 or detachment therefrom—such as the formation or dissolution of complexes, or the like. The process as claimed in the invention and the device 1 as claimed in the invention allow determination of viscosity in this sense.

Alternatively or additionally, with the process as claimed in the invention and the device 1 as claimed in the invention, for example the determination of the Reynolds number and/or the Strouhal number or the like is enabled.

The process as claimed in the invention and the device 1 as claimed in the invention are especially suited also for testing or measuring inhomogeneous fluids 2.

In particular the device 1 is made for microfluidic diagnostics. Preferably the measurement chamber 4 has a volume of at most 1 ml, preferably at most 500 µl, especially at most 100 µl, or from roughly 0.5 to 20 µl.

It should be noted that individual aspects and technical implementations of the explained embodiments and other alternatives which are disclosed in the claims can also be optionally combined with one another.

What is claimed is:

1. Process for determining the viscosity of a fluid, comprising the steps of:
    locating at least one microscopic magnetic particle with an average diameter of from 20 nm to 1.000 microns in a quantity of the fluid,
    moving said magnetic particles in the fluid by means of an inhomogeneous magnetic field,
    setting the said magnetic particles into vibration and translational movement back and forth by variation of the magnetic field over time with an amplitude of at most 1 mm,
    focusing or holding said magnetic particles magnetically in a three-dimensional area within the fluid,
    magnetically measuring by means of lock-in technology at least one of the amplitude and phase of the vibration and determining said viscosity.

2. Process as claimed in claim 1, wherein the magnetic field which varies over time is varied periodically.

3. Process as claimed in claim 1, wherein the magnetic field which varies over time is produced by only one coil or by two coils which are spaced in the direction of vibration.

4. Process as claimed in claim 3, wherein the magnetic fields of the coils are varied periodically.

5. Process as claimed in claim 3, wherein the at least one magnetic particle vibrate is caused to with twice the frequency of the magnetic fields of the coils.

6. Process as claimed in claim 1, wherein the at least one magnetic particle is caused to vibrate with twice the frequency of the magnetic field which varies over time.

7. Process as claimed in claim 1, wherein the magnetic moment of the at least one magnetic particle is aligned by means of a steady-state magnetic field into one direction.

8. Process as claimed in claim 7, wherein the steady-state magnetic field is stronger than the magnetic field which varies over time.

9. Process as claimed in claim 1, wherein the at least one magnetic particle is stabilized by means of diamagnetic shielding in a three-dimensional area in the fluid.

10. Process as claimed in claim 1, wherein the magnetic particles execute induced vibration.

11. Process as claimed in claim 1, wherein the frequency and/or the amplitude and/or the time characteristic of the magnetic field which varies over time is or are controlled such that the amplitude of the vibration of the at least one magnetic particle exceeds a minimum value at least for a definable time interval.

12. Process as claimed in claim 1, wherein the vibration of the at least one magnetic particle is detected by a sensor means which has especially at least one of a measurement coil, a magnetoresistance, a magnetoimpedance, and a Hall sensor.

13. Process as claimed in claim 1, wherein the amplitude and/or the phase of the vibration is or are determined depending on or relative to the varying magnetic field.

14. Process as claimed in claim 1, wherein the at least one magnetic particle is a superparamagnetic particle and/or particle containing iron oxide, especially magnetite or other ferrite, is used.

15. Process as claimed in claim 1, wherein particles with a density at least essentially equal to or greater than the density of the fluid are used.

16. Process as claimed in claim 1, wherein granular, spherical and/or ellipsoidal particles and/or particles with a jacket are used.

17. Process as claimed in claim 1, wherein a fluid volume of less than 1 ml.

18. Device for determining the viscosity of a fluid, comprising:
    a measurement chamber for holding the fluid with at least one coil for producing an inhomogeneous magnetic field which varies over time, so that at least one microscopic magnetic particle with an average diameter from 20 nm to 1.000 microns, completely surrounded by the fluid, can be set into translational vibration within the fluid with an amplitude of at most 1 mm,
    means for focusing or holding said microscopic magnetic particles magnetically in a three-dimensional area within the fluid, and
    at least one of a sensor means and a measurement means for magnetic detection of the vibration of the at least one microscopic magnetic particle, and an evaluation means for determining the viscosity of the fluid.

19. Device as claimed in claim 18, wherein the device is made as a sample carrier, microtiter plate or test strip.

20. Device as claimed in claim 18, wherein the accommodation volume of the device or the measurement chamber for fluid is less than 1 ml.

21. Device as claimed in claim 18, wherein the device is made such that the magnetic field which varies over time can be varied periodically.

22. Device as claimed in claim 18, wherein the device has only one coil or two coils spaced in the direction of vibration for producing the magnetic field which varies over time.

23. Device as claimed in claim 18, wherein the coils are made as Helmholtz coils.

24. Device as claimed in claim 18, wherein the device has a means for producing two magnetic fields which are phase-offset.

25. Device as claimed in claim 18, wherein the means for focusing or holding comprises a means for superimposing a steady-state magnetic field that has a coil or a magnet for producing the steady-state magnetic field in order to align the magnetic moment of the at least one magnetic particle into one direction.

26. Device as claimed in claim 25, wherein the steady-state magnetic field is stronger than the magnetic field which varies over time.

27. Device as claimed in claim 18, wherein the device has diamagnetic shielding in order to stabilize the at least one magnetic particle.

28. Device as claimed in claim 18, wherein the device has a particle-containing measurement chamber for holding the fluid.

29. Device as claimed in claim 28, wherein the measurement chamber is made in a plate-shaped sample carrier.

30. Device as claimed in claim 29, wherein the device is made such that the vibration runs transversely to the flat sides of the sample carrier.

31. Device as claimed in claim 29, wherein coils for producing the magnetic field which is steady-state and/or which varies over time are arranged oppositely on or in the area of the flat sides of the sample carrier.

32. Device as claimed in claim 18, wherein the device has a sensor means for direct detection of the at least one magnetic particle vibration.

33. Device as claimed in claim 18, wherein the at least one magnetic particle is a superparamagnetic particle.

34. Device as claimed in claim 18, wherein said at least one particle is a plurality of magnetic particles and wherein the magnetic particles are at least one of granular, spherical and/or ellipsoidal particles and/or magnetic particles containing iron oxide.

35. Device as claimed in claim 18, wherein the at least one magnetic particle comprises at least one magnetic particle with a jacket.

36. Device as claimed in claim 18, wherein the device is made for accommodating blood or blood plasma as the fluid.

37. Device as claimed in claim 36, wherein the device has a particle-containing measurement chamber for holding the fluid, and wherein the measurement chamber contains the at least one magnetic particle and a coagulation agent so that after supplying blood or blood plasma coagulation can be measured or detected by determination of the viscosity.

38. Device for determining at least one of the viscosity and an associated quantity of a fluid or of microscopic particles in the fluid, comprising:

a measurement chamber for holding the fluid with at least one coil for producing an inhomogeneous magnetic field which varies over time, so that at least one magnetic particle within the fluid, which particle is completely surrounded by the fluid, can be set into translational vibration within the fluid, and at least one of a sensor means and a measurement means for magnetic detection of the at least one magnetic particle vibration having at least one of a measurable amplitude and phase for determining at least one of the viscosity and the associated quantity or the attenuation of particle vibration;

wherein the device has a measurement chamber with a glucose-sensitive fluid which contains magnetic particles, and a membrane which is permeable to glucose, and blood or blood plasma or interstitial liquid can be supplied to the device so that the blood or blood plasma or the interstitial liquid can be brought into glucose exchange by the membrane with the glucose-sensitive fluid and by determining the viscosity of the glucose-sensitive fluid the glucose content in the blood or blood plasma or in the interstitial liquid can be detected and measured.

* * * * *